(12) United States Patent
Marnfeldt et al.

(10) Patent No.: US 8,065,019 B2
(45) Date of Patent: Nov. 22, 2011

(54) METHODS AND SYSTEMS FOR IMPROVING THE RELIABILITY OF THE TIME BASIS FOR DATA LOGGED IN AN IMPLANTABLE MEDICAL DEVICE

(75) Inventors: Goran N. Marnfeldt, Hollviken (SE); Jordi Parramon, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 475 days.

(21) Appl. No.: 12/272,861

(22) Filed: Nov. 18, 2008

(65) Prior Publication Data
US 2010/0125316 A1    May 20, 2010

(51) Int. Cl.
*A61N 1/00* (2006.01)
(52) U.S. Cl. ............................................. 607/60
(58) Field of Classification Search ............... 607/60
See application file for complete search history.

(56) References Cited

U.S. PATENT DOCUMENTS

| | | | |
|---|---|---|---|
| 5,387,229 A | 2/1995 | Poore | |
| 5,776,168 A | 7/1998 | Gunderson | |
| 6,389,315 B1 | 5/2002 | Schu et al. | |
| 6,516,227 B1 | 2/2003 | Meadows et al. | |
| 6,668,194 B2 | 12/2003 | VanHout | |
| 6,741,885 B1 | 5/2004 | Park et al. | |
| 6,985,088 B2 | 1/2006 | Goetz et al. | |
| 7,023,359 B2 | 4/2006 | Goetz et al. | |
| 7,212,133 B2 | 5/2007 | Goetz et al. | |
| 7,317,941 B2 | 1/2008 | Stomberg et al. | |
| 2002/0087146 A1 | 7/2002 | Schu et al. | |
| 2003/0014084 A1 | 1/2003 | VanHout | |

(Continued)

FOREIGN PATENT DOCUMENTS
WO    9736647    10/1997
(Continued)

OTHER PUBLICATIONS

International Searching Authority (EPO), Invitation to Pay Additional Fees and, Where Applicable, Protest Fee for corresponding PCT Application PCT/US2009/052699, Nov. 5, 2009.

*Primary Examiner* — George Manuel
(74) *Attorney, Agent, or Firm* — Wong, Cabello, Lutsch, Rutherford & Brucculeri, LLP

(57) ABSTRACT

Disclosed are methods for synchronizing the time basis of logged data between an implantable medical device such as an IPG and an external device. The IPG logs various operational parameters as data and associates the same with a possibly-inaccurate IPG time stamp and a sequence number. Periodically, the external device sends accurate true time data to the IPG, which, like the operational parameter data, is logged with an IPG time stamp and a next sequence number. The IPG then orders the data sequences and timing sequences by time stamp in a combined data log, and divides that data log into regions in accordance with reset conditions apparent in the time stamp data. Slopes indicative of the relation between true time and time stamps are calculated for various regions on an intra-region or inter-region basis, which then allows for true time estimates to be calculated for the data sequences, thus providing an accurate time basis for the logged data. The true time estimates for the data sequences may then be transmitted from the IPG to an external device for interpretation.

35 Claims, 10 Drawing Sheets

U.S. PATENT DOCUMENTS

| | | |
|---|---|---|
| 2003/0114898 A1 | 6/2003 | Von Arx et al. |
| 2003/0174066 A1 | 9/2003 | Goetz et al. |
| 2003/0174069 A1 | 9/2003 | Goetz et al. |
| 2005/0103351 A1 | 5/2005 | Stomberg et al. |
| 2006/0038701 A1 | 2/2006 | Goetz et al. |
| 2006/0241697 A1 | 10/2006 | Libbus et al. |
| 2007/0097719 A1 | 5/2007 | Parramon |
| 2007/0208232 A1 | 9/2007 | Kovacs |
| 2007/0208233 A1 | 9/2007 | Kovacs |
| 2007/0208262 A1 | 9/2007 | Kovacs |
| 2009/0088821 A1 * | 4/2009 | Abrahamson .................. 607/60 |

FOREIGN PATENT DOCUMENTS

| | | |
|---|---|---|
| WO | 0162142 A2 | 8/2001 |
| WO | 0162142 A3 | 8/2001 |
| WO | 03077993 A1 | 9/2003 |
| WO | 03077995 A1 | 9/2003 |
| WO | 2005049134 A1 | 6/2005 |
| WO | 2006115868 A1 | 11/2006 |
| WO | 2006118499 A1 | 11/2006 |
| WO | 2007103835 A2 | 9/2007 |

* cited by examiner

| Sequence # | Time Stamp | Data | True Time |
|---|---|---|---|
| 99 | 1000 | n/a | 13-SEP-08 – 20:03:56 (t1) |
| 100 | 1234 | D0 | ? |
| 101 | 1256 | D1 | ? |
| 102 | 1278 | D2 | ? |
| 103 | 2123 | n/a | 14 SEP 08 – 07:13:00 (t2) |
| 104 | 2345 | D3 | ? |
| 105 | 2 | D4 | ? |
| 106 | 6 | n/a | 14 SEP 08 – 08:23:12 (t3) |
| 107 | 11 | D5 | ? |
| 108 | 3 | D6 | ? |
| 109 | 27 | D7 | ? |
| 110 | 2 | D8 | ? |
| 111 | 8 | n/a | 14 SEP 08 – 08:32:10 (t4) |
| 112 | 70 | D9 | ? |
| 113 | 102 | n/a | 14 SEP 08 – 10:06:08 (t5) |
| 114 | 234 | n/a | 14 SEP 08 – 13:52:50 (t6) |

*Figure 5*

METHODS AND SYSTEMS FOR IMPROVING THE RELIABILITY OF THE TIME BASIS FOR DATA LOGGED IN AN IMPLANTABLE MEDICAL DEVICE

FIELD OF THE INVENTION

The present invention relates to synchronizing the time basis of data between an implantable medical device and an external device.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227, which is incorporated herein by reference in its entirety. However, the present invention may find applicability in any implantable medical device system. For example, the disclosed invention can also be used with a Bion™ implantable stimulator, such as is shown in U.S. Patent Publication 2007/0097719, filed Nov. 3, 2005, which is also incorporated herein by reference in its entirety.

As shown in FIGS. 1A and 1B, a SCS system typically includes an Implantable Pulse Generator (IPG) 100, which includes a biocompatible case 30 formed of titanium for example. The case 30 typically holds the circuitry and power source or battery necessary for the IPG to function, although IPGs can also be powered via external RF energy and without a battery. The IPG 100 is coupled to electrodes 106 via one or more electrode leads (two such leads 102 and 104 are shown), such that the electrodes 106 form an electrode array 110. The electrodes 106 are carried on a flexible body 108, which also houses the individual signal wires 112 and 114 coupled to each electrode. In the illustrated embodiment, there are eight electrodes on lead 102, labeled $E_1$-$E_8$, and eight electrodes on lead 104, labeled $E_9$-$E_{16}$, although the number of leads and electrodes is application specific and therefore can vary.

As shown in FIG. 2, the IPG 100 typically includes an electronic substrate assembly 14 including a printed circuit board (PCB) 16, along with various electronic components 20, such as microprocessors, integrated circuits, and capacitors mounted to the PCB 16. Two coils are generally present in the IPG 100: a telemetry coil 13 used to transmit/receive data to/from an external controller 12 as explained further below; and a charging coil 18 for charging or recharging the IPG's power source or battery 26 using an external charger (not shown). The telemetry coil 13 can be mounted within the header connector 36 of the IPG 100 as shown.

As just noted, an external controller 12, such as a hand-held programmer or a clinician's programmer, is used to send data to and receive data from the IPG 100. For example, the external controller 12 can send programming data to the IPG 100 to dictate the therapy the IPG 100 will provide to the patient. Also, the external controller 12 can act as a receiver of data from the IPG 100, such as various data reporting on the IPG's status. The external controller 12, like the IPG 100, also contains a PCB 70 on which electronic components 72 are placed to control operation of the external controller 12. A user interface 74 similar to that used for a computer, cell phone, or other hand held electronic device, and including touchable buttons and a display for example, allows a patient or clinician to operate the external controller 12.

Wireless data transfer between the IPG 100 and the external controller 12 takes place via inductive coupling. To implement such functionality, both the IPG 100 and the external controller 12 have coils 13 and 17 respectively. Either coil can act as the transmitter or the receiver, thus allowing for two-way communication between the two devices. When data is to be sent from the external controller 12 to the IPG 100 for example, coil 17 is energized with alternating current (AC), which generates a magnetic field 29, which in turn induces a voltage in the IPG's telemetry coil 13. The generated magnetic field 29 is typically modulated using a communication protocol, such as a Frequency Shift Keying (FSK) protocol, which is well known in the art. The power used to energize the coil 17 can come from a battery 76, which like the IPG's battery 26 is preferably rechargeable, but power may also come from plugging the external controller 12 into a wall outlet plug (not shown), etc. The induced voltage in coil 13 can then be demodulated at the IPG 100 back into the telemetered data signals. To improve the magnetic flux density, and hence the efficiency of the data transfer, the IPG's telemetry coil 13 may be wrapped around a ferrite core 13'.

As is well known, inductive transmission of data from coil 17 to coil 13 can occur transcutaneously, i.e., through the patient's tissue 25, making it particular useful in a medical implantable device system. During the transmission of data, the coils 13 and 17 lie in planes that are preferably parallel. Such an orientation between the coils 13 and 17 will generally improve the coupling between them, but deviation from ideal orientations can still result in suitably reliable data transfer.

As mentioned previously, the IPG 100 can communicate various types of status data back to the external controller 12, such as the voltage of the battery 26 (Vbat) and other operational parameters of interest. Typically, such operational parameters are read and stored by the IPG 100 on a schedule, such as every ten minutes or so. Thereafter, the stored data may be communicated back to the external controller 12 at an appropriate opportunity (such as when the external controller 12 requests communication with the IPG 100), or may be queried by the IPG 100 for its own internal use as appropriate. Typically, such data is stored in a non-volatile memory, such as a flash EPROM memory, so that the data is preserved in the event that the IPG 100 looses power, such as when the battery 26 becomes depleted. Transfer of stored data back to the external controller 12 can allow the user or a clinician to interpret the stored data to some useful end, and such analysis may require connection between the external controller 12 and a computer (not shown).

Operational parameter data is also typically stored in the IPG 100 with a time stamp, which comprises the IPG's understanding of the time that particular data was logged. A time stamp usually comprises a numeric (e.g., binary) value determined by the IPG's internal timing circuitry. Such timing circuitry usually operates in conjunction with the IPG's clocking circuitry, and may be based upon a simple clock pulse counter to cite one simple example.

Unfortunately, the time stamp associated with the stored data can be unreliable for at least two reasons. First, the IPG's timing circuitry may be inherently inaccurate, such that the time stamps deviate from true time by an unacceptable margin. Second, and perhaps most significantly, loss of power in the IPG 100 can cause the timing circuitry to reset. For example, suppose the battery 26 in the IPG becomes so depleted that the IPG's timing circuitry can no longer operate. Although the battery 26 can be recharged and the timing circuitry later enabled, the timing circuitry will have lost its timing reference. Thus, after coming up from a reset condition, the IPG 100's timing circuitry would understand the IPG to be operating at "time zero," and would incorrectly start stamping logged data accordingly.

The inability to properly establish an accurate time basis for logged IPG data hampers the utility of such logged data, because certain logged data may only be useful when judged against an accurate time basis. To cite just one example, it may be important to assess battery voltage as a function of real time, because the rate of any degradation may be an important factor in determining when the IPG's battery 26 needs to be replaced (by explanting the IPG 100 from the patient). Without an accurate time basis, such battery voltage data, and other time-sensitive operational parameter data, may be of limited use.

Accordingly, it would be beneficial to improve the reliability of the time basis for data logged in an implantable medical device such as an IPG 100. This disclosure presents such solutions.

BRIEF DESCRIPTION OF THE DRAWINGS

FIG. 5 shows the combination of the data log of FIG. 3 and the true time log of FIG. 4 into a combined log, and the recognition of different regions in the combined data log.

DETAILED DESCRIPTION

The description that follows relates to use of the invention within a spinal cord stimulation (SCS) system. However, it is to be understood that the invention is not so limited. Rather, the invention may be used with any type of implantable medical device system that could benefit from data logging with a more accurate time basis. For example, the present invention may be used as part of a system employing an implantable sensor, an implantable pump, a pacemaker, a defibrillator, a cochlear stimulator, a retinal stimulator, a stimulator configured to produce coordinated limb movement, a cortical and deep brain stimulator, or in any other neural stimulator configured to treat any of a variety of conditions.

Disclosed are methods for synchronizing the time basis of logged data between an implantable medical device such as an IPG and an external device. The IPG logs various operational parameters as data and associates the same with a possibly-inaccurate IPG time stamp and a sequence number. Periodically, the external device sends accurate true time data to the IPG, which, like the operational parameter data, is logged with an IPG time stamp and a next sequence number. The IPG then orders the data sequences and timing sequences by time stamp in a combined data log, and divides that data log into regions in accordance with reset conditions apparent in the time stamp data. Slopes indicative of the relation between true time and time stamps are calculated for various regions on an intra-region or inter-region basis, which then allows for true time estimates to be calculated for the data sequences, thus providing an accurate time basis for the logged data. The true time estimates for the data sequences may then be transmitted from the IPG to an external device for interpretation.

Figure 3:
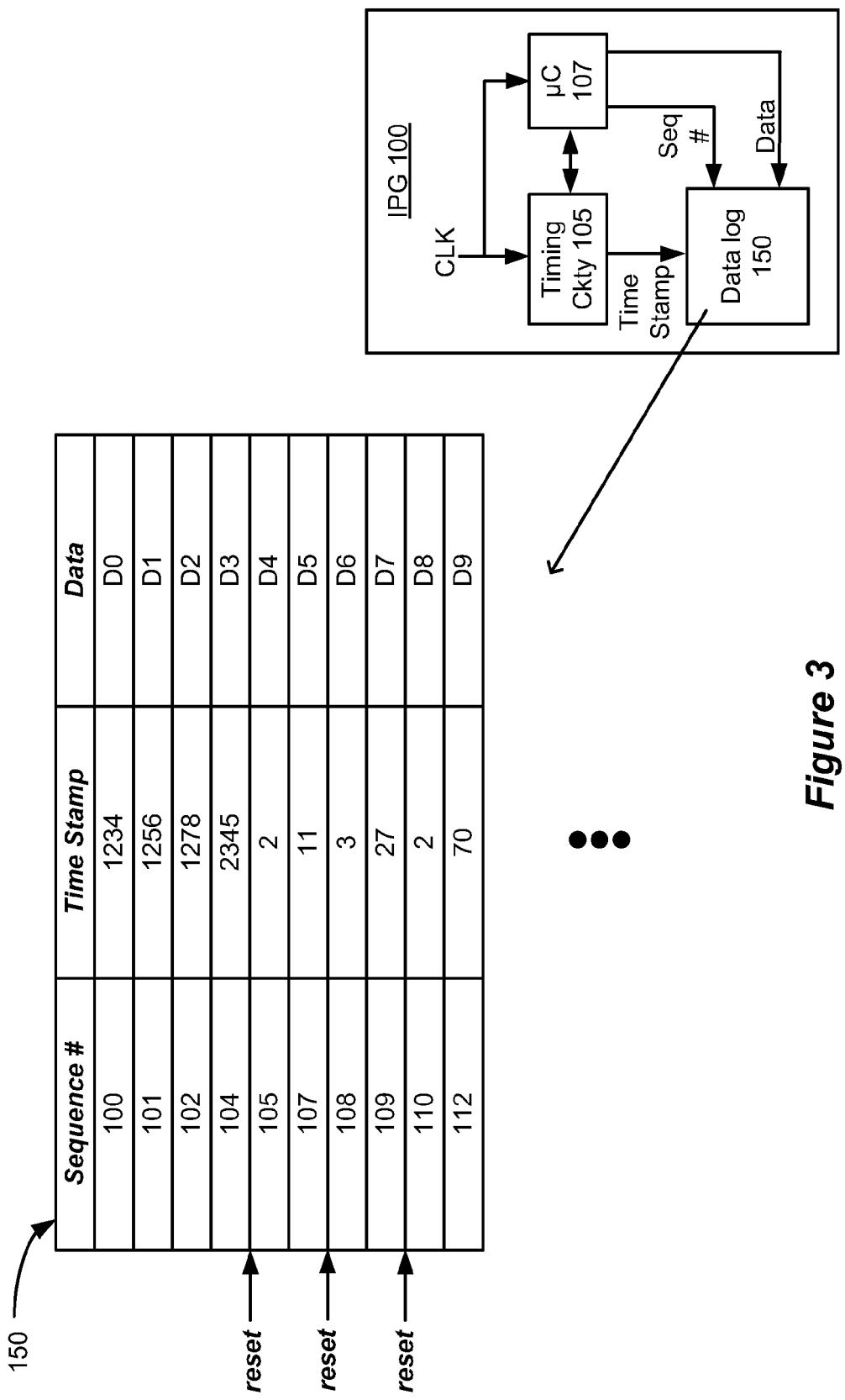
FIG. 3 shows a data log within the IPG, with data values associated with an IPG time stamp and a sequence number.

FIG. 3 shows a data log 150 as stored within the non-volatile memory of an IPG 100. Each row, or "data sequence," corresponds to a particular point in time as understood by the IPG 100 in accordance with a time stamp. Thus, data D0 is associated with time stamp 1234, which might comprise some function of a number of clock pulses counted by the timing circuitry 105 within the IPG 100 as discussed previously in the Background section. Data D1 was stored some time later at time stamp 1256, etc. One can appreciate that data can be logged in accordance with a data logging algorithm, which might specify that data be logged at periodic increments of time. Thus, it can be seen that data D0, D1, and D2 were logged at a periodic interval of 22 time stamps, where a single time stamp might be approximately a second for example. However, the data logging algorithm can also cause the IPG 100 to log data at non-periodic intervals. For example, data D4 was logged more than 1000 time stamps after D3. As alluded to earlier, the data Dx can comprise an operation parameter, a status, a flag, or any other information which might require assessment by external controller 12, and ultimately the patient or clinician.

To organize the relative timing of the various logged data sequences, each sequence is associated with a sequence number, which sequentially increments at each new data logging. Such sequence number can come from the timing circuitry 105, but may also come from the microcontroller 107 operating within the IPG 100 as shown. Thus, D0, stored at time stamp 1234, is assigned sequence number 100. D1, the next data stored at time stamp 1256, is assigned the next sequence number 101, etc. The sequence number, like the logged data, is typically stored in non-volatile memory within the IPG so that value is not lost even in the event of IPG power failure.

As mentioned earlier, the logged data, Dx, may comprise a single operational parameter (e.g., voltage of the battery within the IPG, Vbat) measured at a given point in time. Or, the data can comprise several operation parameters, such that each entry Dx in effect comprises an array of values. If not desired to store multiple parameters in a single data log 150, the IPG 100 may contain several different data logs 150 for each parameter of interest, each operating in accordance with its own data logging algorithm. Typically, the non-volatile memory in which the data log 150 (or logs as the case may be) is stored will have a limited capacity. The limited capacity means that older data will eventually be overwritten by newer data such that the non-volatile memory will hold a few month's worth or perhaps a year's worth of data for a given operational parameter.

As discussed previously, the time basis of the data in data log 150 may not be accurate because it has been reset by a power failure, or for other reasons. FIG. 3 illustrates such inaccuracies. For example, between data sequences 104 and 105 it is noticed that the time stamp has decreased from 2345 to 2; similar decreases in the time stamp appear between data sequences 107 and 108, and 109 and 100. Assuming that the numeric value for the time stamp has no practical upper limit and can increase indefinitely, such a decrease in the time stamp suggests a problem with the time basis of the sequenced data. It can therefore be inferred that a chronological discontinuity (e.g., a reset, a power failure) has occurred in the timing circuitry 105 of the IPG 100 between these time-stamped data sequences, which reset must be rectified if an accurate time basis is desired.

Figure 4:
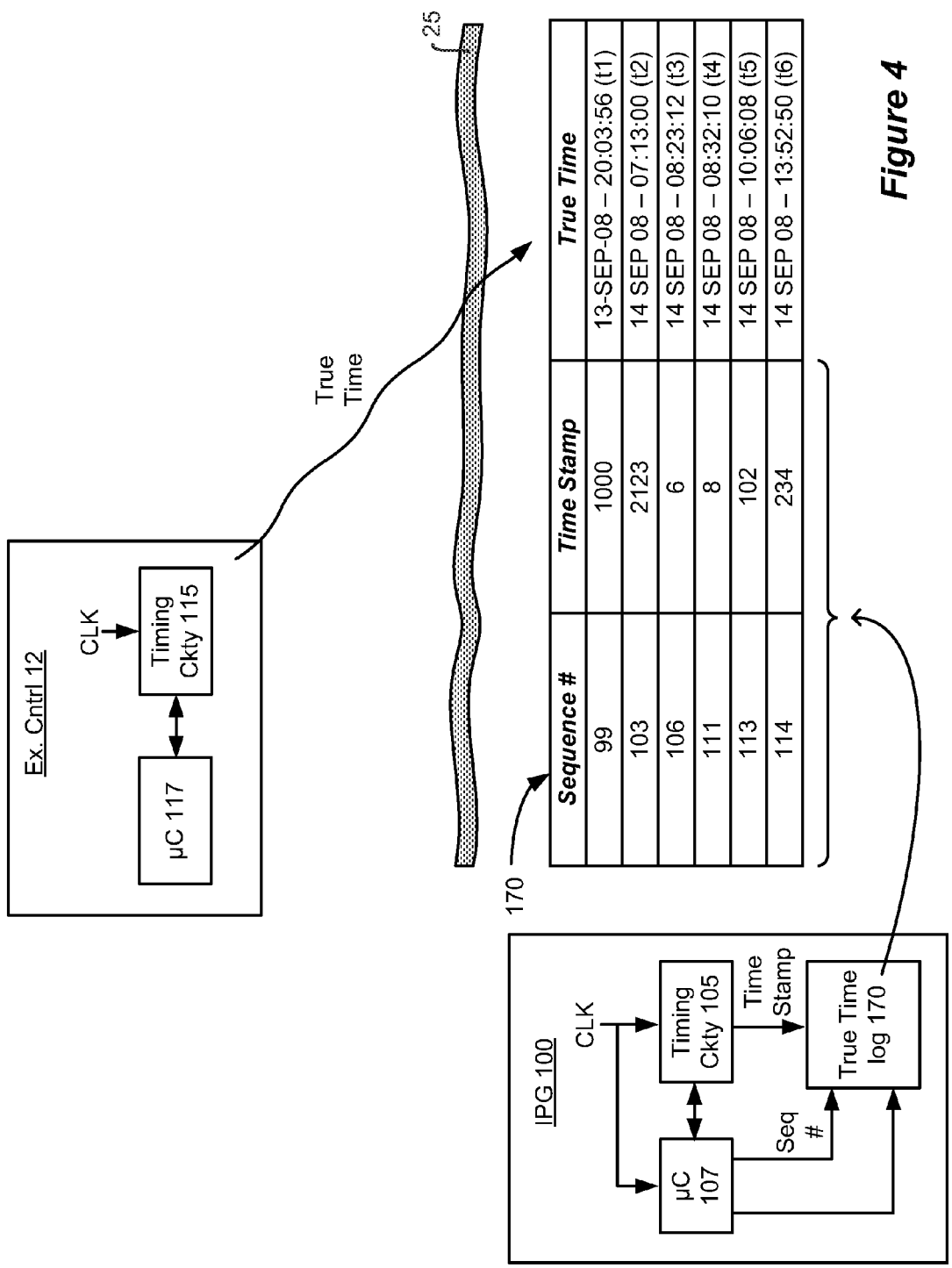
FIG. 4 shows determination of a true time by an external controller 12, transmission of the true time to the IPG, and logging of such true time in a true time data log, wherein each true time is associated with an IPG time stamp and a sequence number.

FIG. 4 shows a true time log 160 effective in rectifying such discontinuities in the IPG's time basis. Shown in FIG. 4 is timing circuitry 115 within the external controller 12 with which the IPG 100 wirelessly communicates. In this embodiment, the timing circuitry 115 in the external controller 12 provides a highly accurate time basis (called "true time" herein) to the IPG 100. In a preferred embodiment, the timing circuitry 115 can comprise a crystal oscillator-based timing circuit, which is highly accurate and well known in the art of electronic devices. Because crystal oscillator-based timing circuits can take up significant volume, use of such circuitry for the timing circuitry 105 within the IPG 100 may not be possible, which is made as small as possible to reduce potential discomfort to the patient in which the IPG is implanted. However, because space within the external controller 12 is more plentiful, the external controller 12 can easily accommodate timing circuitry 115.

As shown in FIG. 4, timing circuitry 115 provides a true time to the IPG 100 at certain times, as controlled by an algorithm operable by the microcontroller 117 in the external controller 12. As shown for illustration purposes, this true time is shown as a date and time. However, in an actual implementation, such true time data would more logically be converted to some sort of binary representation. In recognition of this fact, and for ease of illustration, the true times are denoted chronologically in the Figures as t1, t2, t3, etc. Just like other data, the true time data is wirelessly transmitted by the external controller 12 to the IPG 100 using the data transmission coil 17 (FIG. 2) as discussed in the Background section (but not shown in FIG. 4). The algorithm controlling the transmission of the true time data may dictate, for example, that the true time be sent to the IPG 100 on some reasonable basis. For example, the true time may be sent by the external controller 12 to the IPG 100 when communication is initiated between external controller 12 and the IPG 100 for some other purpose. Optionally, the algorithm may send the true time only if true time was not recently sent, for example, in the last two hours. Placing such limitations on the true time algorithm prevents the true time from being sent needlessly excessively.

Once wirelessly received by the IPG 100, the microcontroller 107 in the IPG 100 stores the received true time in a true time log 170 as shown in FIG. 4. Specifically, the true time in the illustrated example is treated by the IPG 100 as data, and is logged similarly to the manner in which data Dx is logged in data log 150 (FIG. 3). Thus, on reception of the true time data, the IPG 100 logs the true time along with a time stamp as provided by its timing circuitry 105 (which as previously mentioned may be inaccurate), and a sequence number as provided by its microcontroller 107, such that each row in the true time log 170 comprises a timing sequence. Because sequence numbers are also sequentially assigned to the data sequences in the data log 150 (FIG. 3), gaps are noticeable in the sequence numbers in the true time log 170, with the missing sequence numbers (e.g., 100, 101, 102, 104, etc.) corresponding to data sequences in the data log 150. As with the data log 150, the true time log is preferably stored in non-volatile memory in the IPG 100.

Thereafter, the data log 150 and the true time log 170 are combined to create a combined log 180 as shown in FIG. 5. In the combined log 180, data sequences from the data log 150 and timing sequences from the true time log 170 are combined and ordered by sequence number. Note that timing sequences have no corresponding data (shown as 'n/a' in the combined log 180), while data sequences (at this point) have no corresponding true time (shown as '?').

It is worth noting at this point that it is not necessary to the disclosed technique to have the IPG 100 separately compile a data log 150 and true time log 170, and then as a separate step to combine those logs to create the combined log 180. Instead, combined log 180 could be directly populated with data and timing sequences in chronological order, with each new sequence being stored at a next address in the flash memory. In such an implementation, it may not be strictly necessary to additionally store or track the sequence numbers in the memory, as the sequential addresses can substitute for such sequence numbers and can ensure the chronology of the sequences. Although direct population of combined log 180 may comprise a more logical manner of implementing the technique, illustration of separate data and true time logs (150, 170) and their combination (180) are shown in the Figures because it is believed to illustrate the technique with more clarity.

Regardless of how combined log 180 is compiled, a goal of the technique is associate the data entries Dx with an accurate time basis. In one embodiment, such an accurate time basis is interpolated or extrapolated using both the true time data and the time stamps in combined log 180. Simply said, a goal of the technique is to estimate a true time for the data entries.

One way of achieving this goal is illustrated in FIG. 5 and begins with identification of the discontinuities (e.g., resets) appearing in the IPG's time stamp data. As mentioned previously, such reset conditions can be identified by a decrease in the time stamp. Thus, in FIG. 5, a reset condition is identified between sequences 104 and 105; 107 and 108; and 109 and 110. Identification of such reset conditions is easily performed by the microcontroller 107 in the IPG 100 upon reviewing the combined data log 180.

Figure 6:
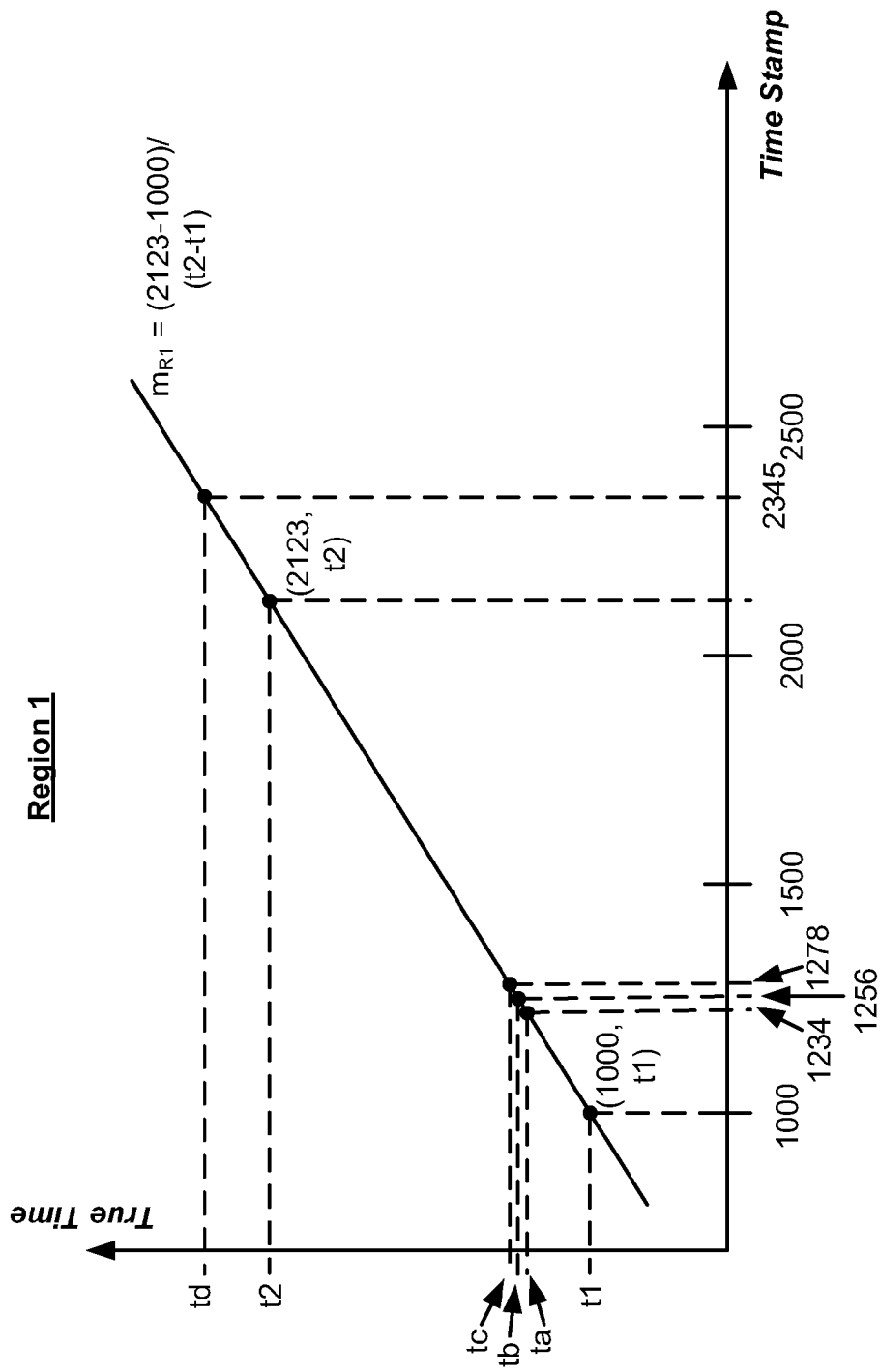
FIGS. 6-8 show the estimation of the true time of data sequences for differing regions in the combined log.
Figure 9:
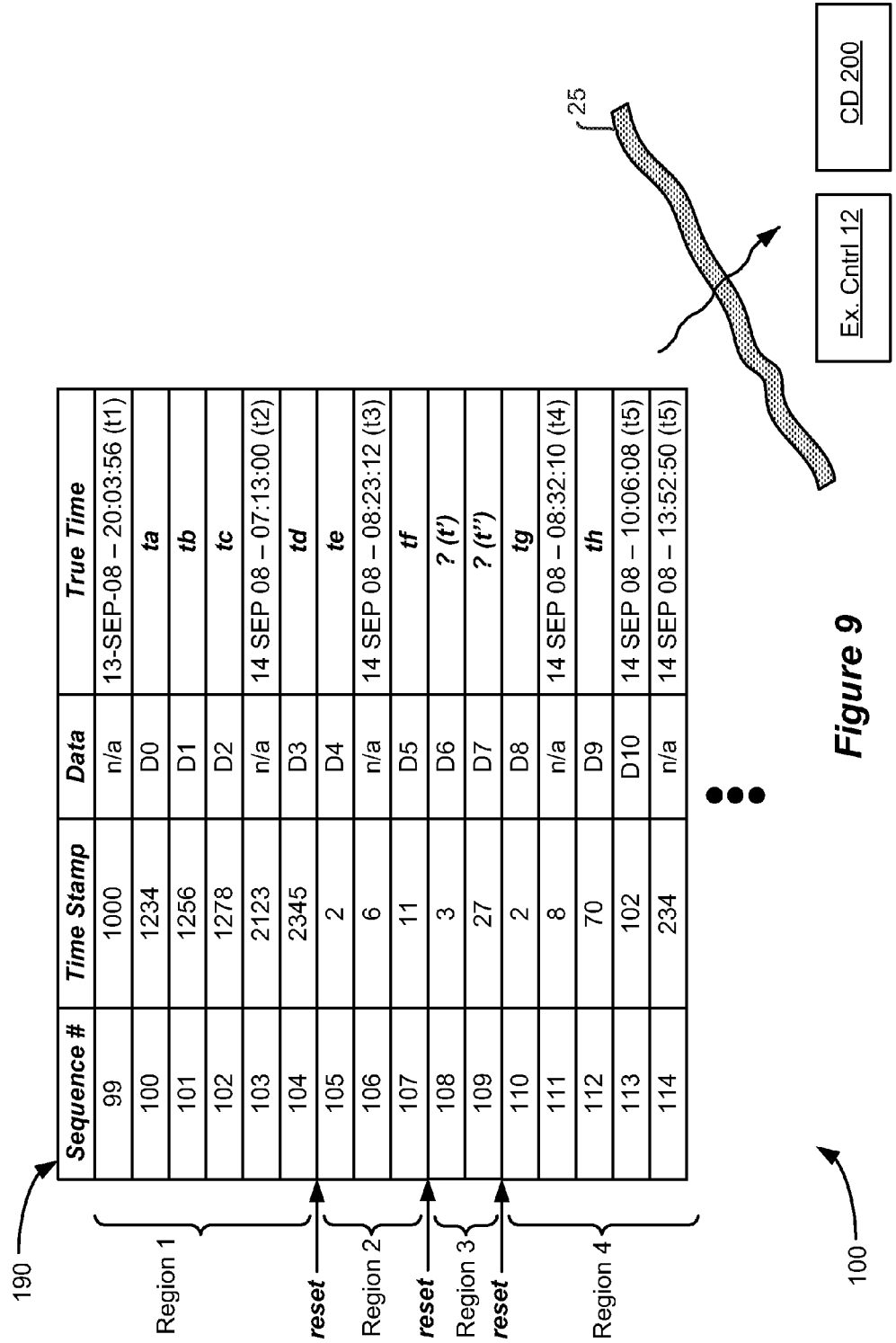
FIG. 9 shows compilation of an estimated true time log and transmission of that log to an external device.

The sequences between the resets can then be considered as regions, which regions can be considered separately or together to interpolate or extrapolate an accurate time basis for the data. Such interpolation or extrapolation comes from establishing a relationship between the true time and the time stamps in each of the regions. Consider Region 1 in FIG. 5. In this region there are two true time stamps (t1 and t2) for sequences 99 and 103. Because both true time and the time stamps should be linear (even if inaccurate), a linear relationship can be determined between the two within that region, which is shown in FIG. 6 as a plot of time stamp versus true time. Here, time stamp and true time values for timing sequences 99 (1000, t1) and 103 (2123, t2) are plotted, which allows a slope to be determined ($m_{R1}$=2123−1000/t2−t1) and applied to the data sequences (100, 101, 102, and 104) in Region 1. Thus, time stamps 1234, 1256, and 1278 for data sequences 100, 101, and 102 can be interpolated to true times ta, tb, and tc respectively using slope $m_{R1}$. Time stamp 2345 for data sequence 104 can likewise be extrapolated to true time td. In so doing, the estimated true time data ta, tb, tc, and td for Region 1 can be added to the combined log 180 to form an accurate-time-basis data log 190 as shown in FIG. 9.

Referring again to FIG. 5, it can be seen that Region 4 has three timing sequences (111, 113, and 114) having both a time stamp and a true time (8, t4; 102 t5; and 234, t6, respectively).

Figure 7:
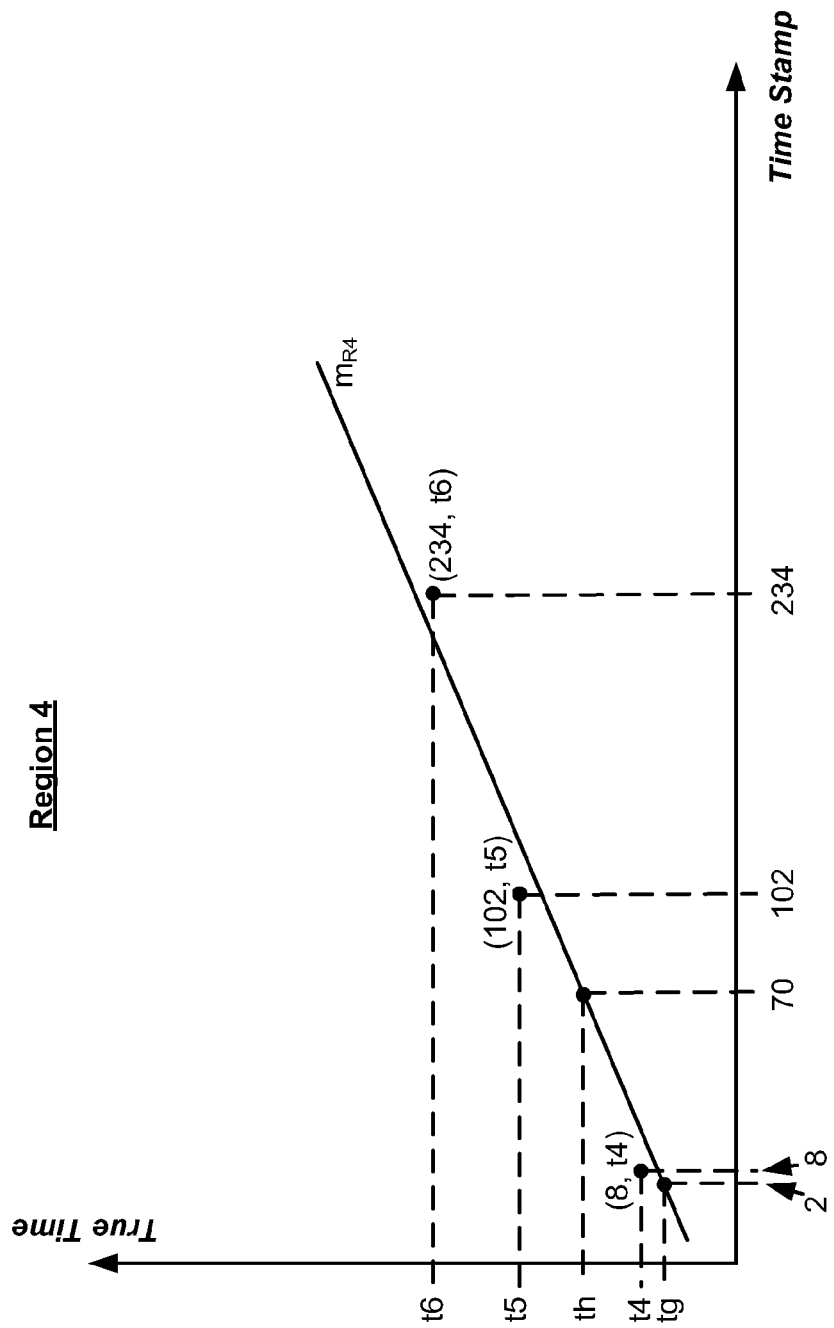

These three data points can be used to determine a slope ($m_{R4}$) to help estimate true time for the data sequences (110 and 112) appearing in this region. This is shown graphically in FIG. 7. In this case, the existence of three points having both time stamp and true time data can make the determination of slope more accurate, and more complex. For example, a least squares or other fitting algorithm can be used by the microcontroller 107 in the IPG 100 to calculate the slope, $m_{R4}$, of a best-fit line between these three points. From this slope $m_{R4}$, true times corresponding to the time stamps for sequences 110 and 112 (tg, th) can be estimated, and populated in the accurate-time-basis data log 190 of FIG. 8.

Figure 8:
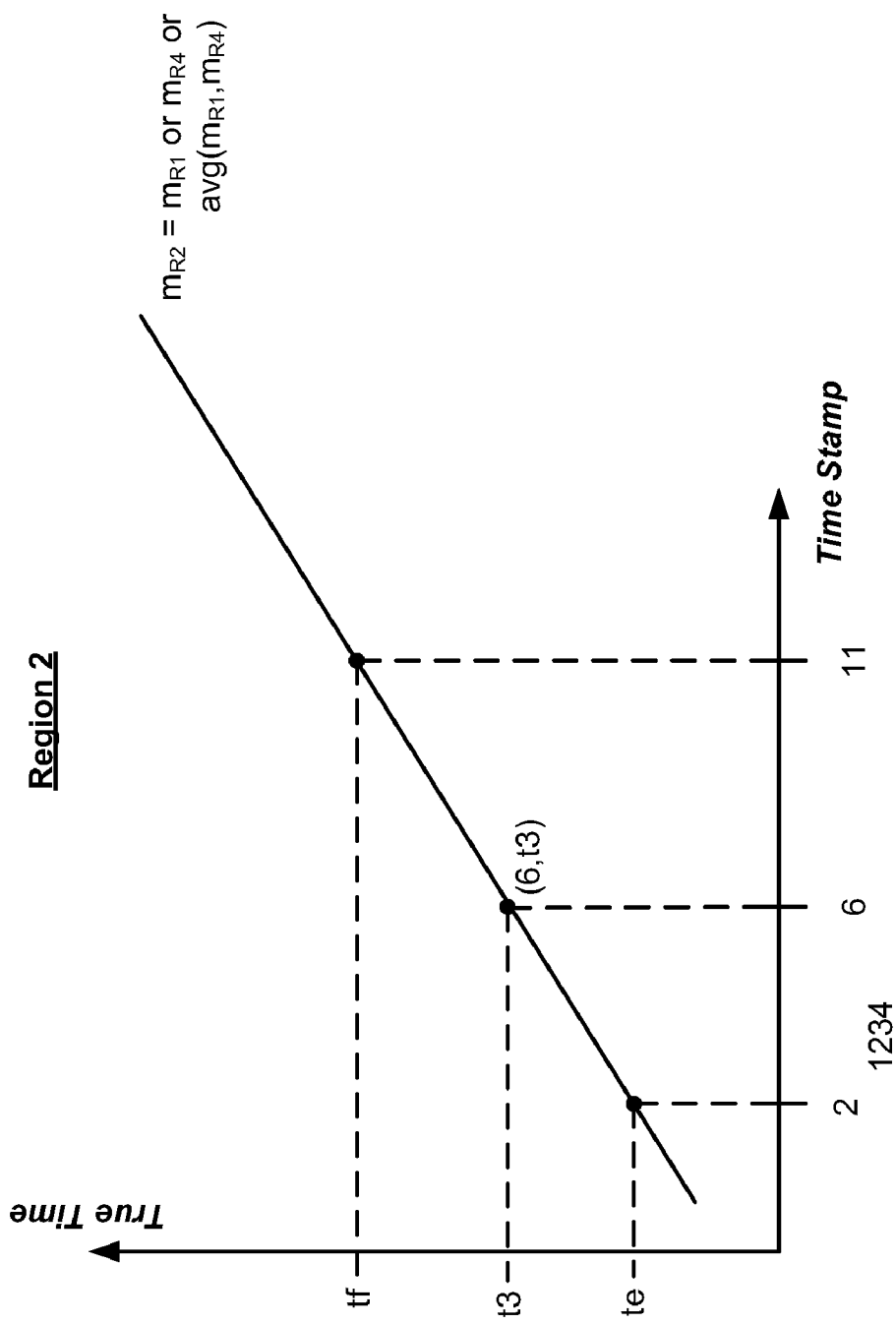

In the foregoing examples, estimation of an accurate time basis for the data sequences in a given region occurred using only data from within that region, i.e., an intra-region estimation approach. However, time basis estimation can also occur using data from other regions, or from multiple regions, i.e., an inter-region approach. Consider Region 2 as shown in FIG. 5. This region contains only one timing sequence (106) having both a time stamp and a true time (6, t3). A slope for Region 2 cannot be estimated using only a single point's worth of data, and so an intra-region approach cannot be employed. Therefore, an inter-region approach is used in this region, as illustrated in FIG. 8. As shown, at least one slope from another region can be used to establish the correlation between the true time and the time stamps, such as Region 1 ($m_{R1}$) or Region 4 ($m_{R4}$). In other words, the slope in Region 2 ($m_{R2}$) can be set to $m_{R1}$, $m_{R4}$, some average of the two, or an average from all of the regions in which a slope can be reliably determined, etc. Once $m_{R2}$ is established in this way, that slope may be applied to the single known point (6, t3), and used to estimate the true time for the other two data sequences 105 and 107 (te, tf) in Region 2, which times may then be populated in the accurate-time-basis data log 190 of FIG. 9.

Referring again to FIG. 5, it can be seen that Region 3 has only two data sequences (108 and 109), neither of which is associated with a true time. Without a single point of correlation in the region, the true times for these sequences cannot be estimated using the intra- (FIG. 6 or 7) or inter- (FIG. 8) region approaches so far disclosed, although further analysis may provide allow for a rough estimate, as will be discussed further below. For the time being therefore, it is assumed that true times cannot be estimated for these sequences 108 and 109, and they are therefore shown in FIG. 9 as indeterminate values ('?').

Figure 10:
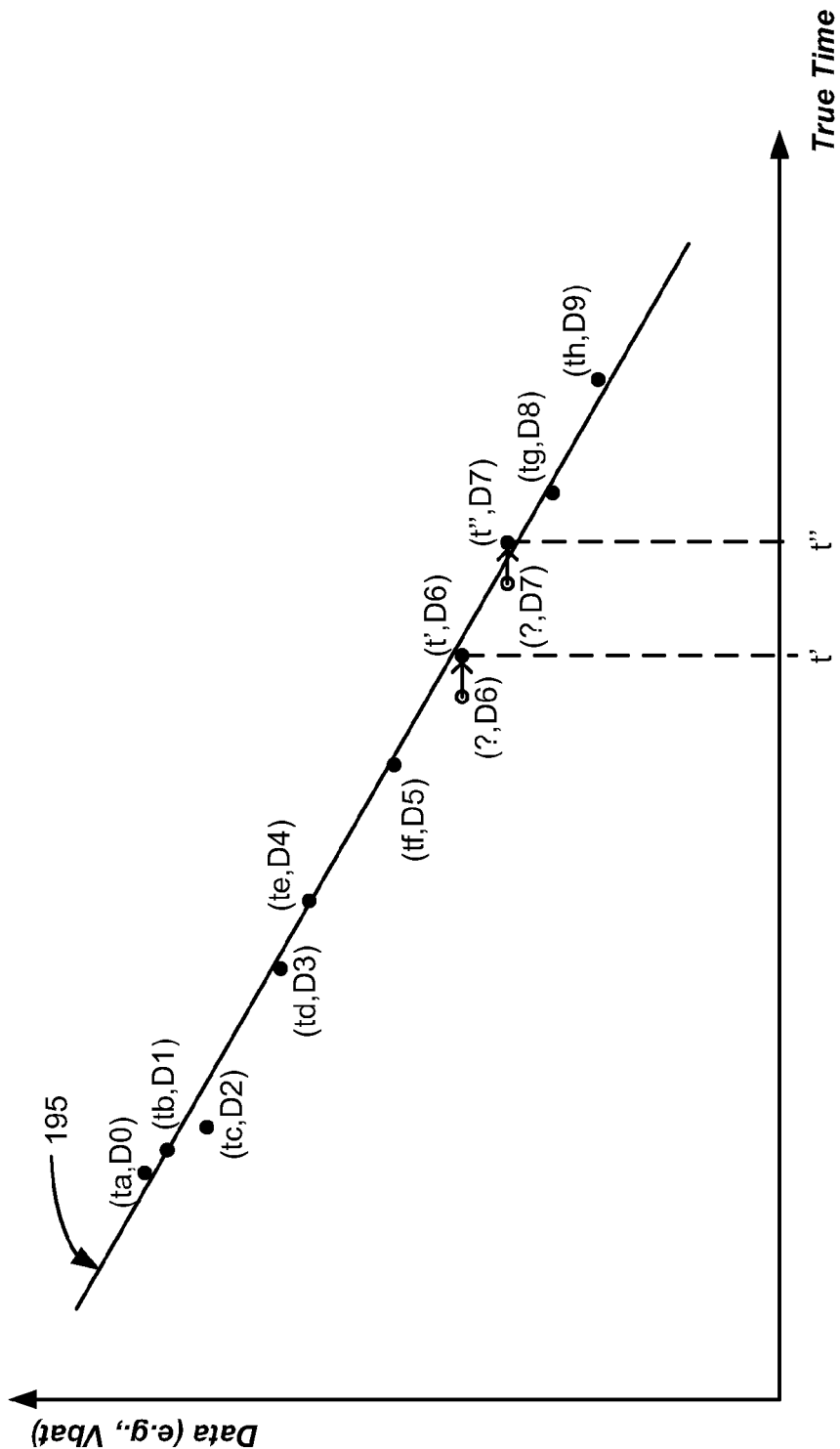
FIG. 10 shows analysis of a particular data value as a function of the estimated true time.

With the accurate-time-basis data log 190 so populated as shown in FIG. 9, the data within that log has a more accurate time basis that that provided by the IPG's time stamps alone, and furthermore has a time basis fixed with respect to reset conditions. This is depicted in FIG. 10, which shows a plot of a given logged data value as a function of estimated true time, for example, the IPG's battery 26 voltage, Vbat. As illustrated, the battery voltage in this example is decreasing at a relatively constant rate over time. Also seen are the data values (D6 and D7) for the sequences (108 and 109) in Region 3 whose true time remained indeterminate. Such indeterminacy makes it unclear where these particular data points occur in time, and so are shown as unfilled circles in FIG. 10.

It may be perfectly acceptable to simply disregard the indeterminate data points in the accurate-time-basis data log 190, particularly if there are enough other reliable data points to provide a proper understanding of the particular data value over time. Otherwise, the timing for these indeterminate data points may be estimated using a best fit line 195 that correlates the data value to the true time. (This of course assumes the data comprises a numerical value as opposed to a status indicator, flag, etc.). In the illustrated example, the indeterminate data points are thus translated in time (to keep their timing relative to one another) and fit to the best fit line 195 (corresponding to the filled circles), which allows their true time values (t' and t") to be estimated. Such estimated true time values t' and t" can then be populated into the accurate-time-basis data log 190 as shown in FIG. 9 if desired. Again, this may not be necessary and the accurate-time-basis data log 190 can instead merely retain the indeterminate true times for the affected data values D6 and D7.

Figures 1A, 1B:
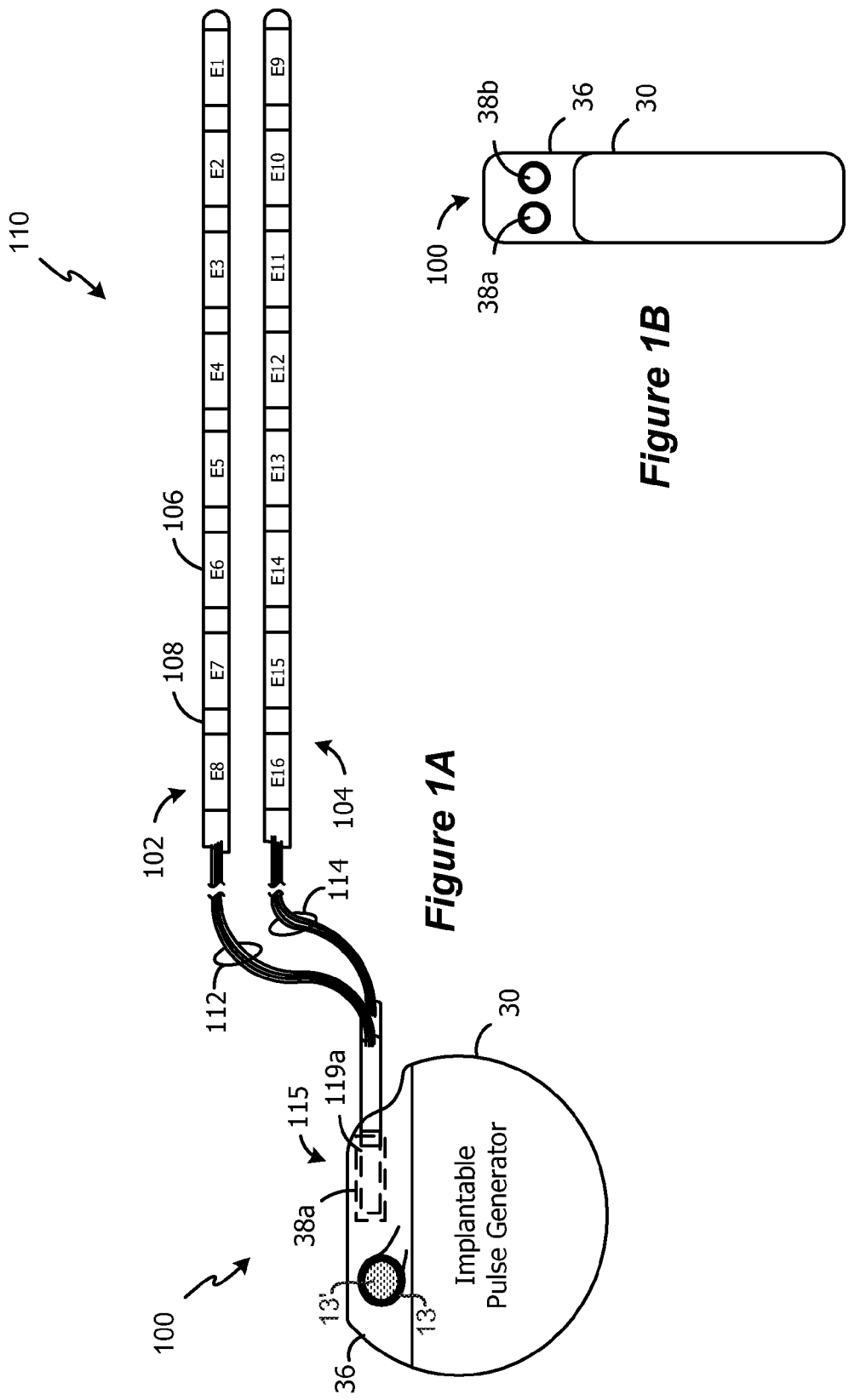
FIGS. 1A and 1B show an implantable pulse generator (IPG), and the manner in which an electrode array is coupled to the IPG in accordance with the prior art.
Figure 2:
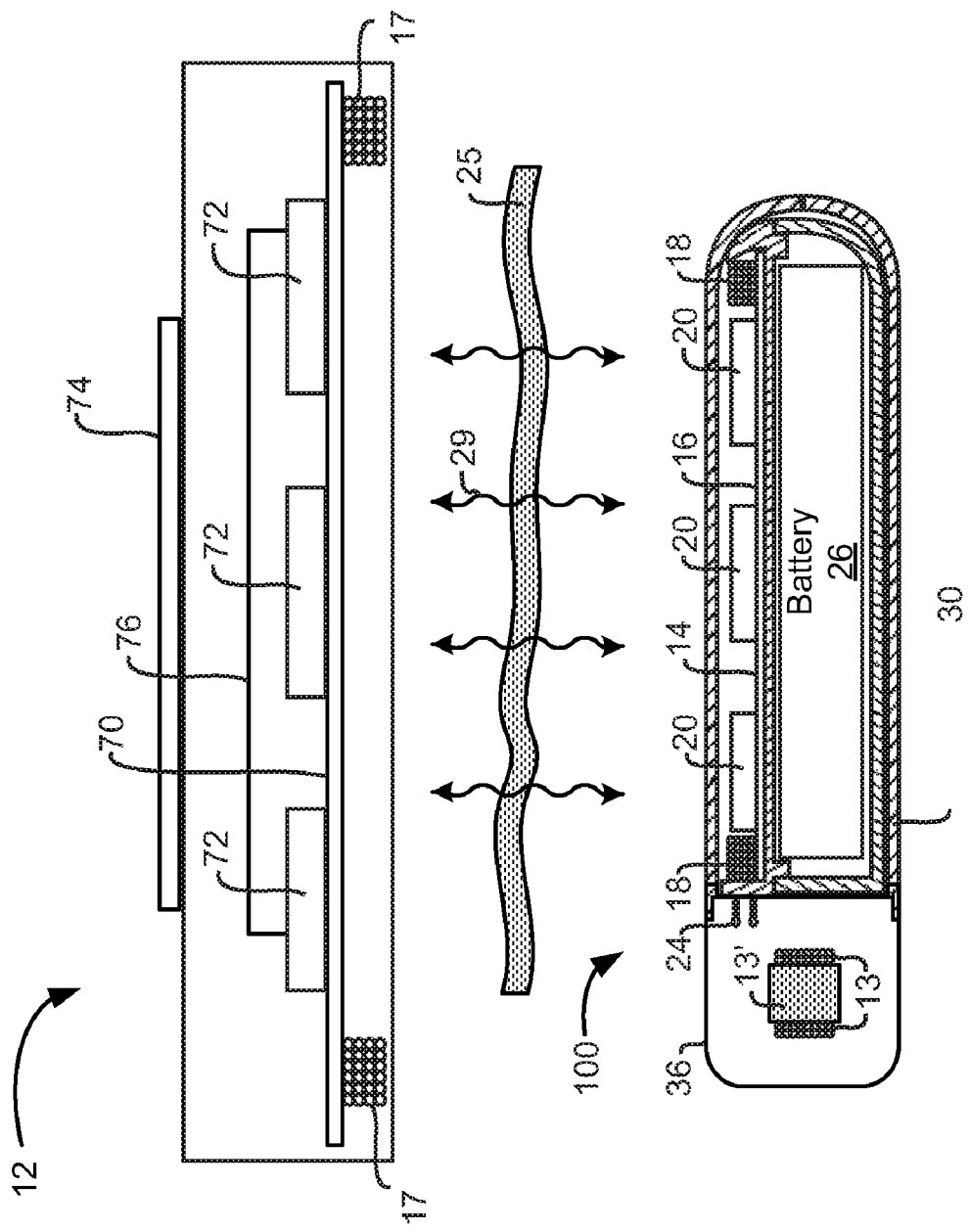
FIG. 2 shows the relation between the IPG and an external controller with which it communicates via electromagnetic inductive coupling.

Referring again to FIG. 9, it can be seen that the IPG 100 can wirelessly transmit the accurate-time-basis data log 190 to the external controller 12 via its data coil (13; FIG. 2). This can allow the log 190 to be assessed by the patient or doctor at the external controller 12, to allow particular data values to be graphed and display on the user interface 74 of the external controller 12, etc. Should the external controller 12's analytical power be lacking or its user interface 74 unacceptable to allow for proper interpretation of the data values, the log 190 can likewise be transmitted to a more sophisticated clinician device 200, which may comprise a clinician's programmer, a personal computer, or the like. Alternatively, the accurate-time-basis data log may not be transmitted at all, but may be retained for interpretation by the IPG 100.

To this point, it has been assumed true time estimates are calculated in the IPG 100. In other words, it has been assumed that the microprocessor 107 and associated programs within the IPG 100 operate to assess the combined log 180 and to determine the accurate-time-basis data log 190. However, this is not strictly necessary, and such computations may be moved to the external controller 12, the clinician device 200, or elsewhere outside of the IPG 100. For example, the combined data log 180 may be wirelessly transmitted to the external controller 12, at which point, algorithms operable in the external controller 12 in conjunction with its microcontroller 117 would assess the various regions in the data; determine the proper slopes for the various regions to allow the true times for the data sequences to be estimated to form the accurate-time-basis data log 190, etc. In short, it is not particularly important where in the system the true times for the data sequences are estimated.

As illustrated, the true time data comes from the external controller 12. However, the invention is not so limited. For example, the true time could be wirelessly transmitted from any device external to the patient, such as a charging device (for recharging the IPG's battery 26), a clinician's device, etc. Such an external device need not comprise a hand held device, but instead could comprise a desktop computer or similar external data system or server.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method implementable in an implantable medical device, the method comprising:

obtaining data in the implantable medical device at various points in time;

associating each obtained data with an inaccurate time stamp provided by the implantable medical device;

receiving at the implantable medical device first accurate times from an external device at various points in time; and estimating second accurate times for each obtained data using the first accurate times.

2. The method of claim 1, wherein the time stamps are inaccurate because they contain chronological discontinuities indicative of reset conditions in the implantable medical device, and wherein the second accurate times do not contain chronological discontinuities.

3. The method of claim 1, further comprising wirelessly transmitting at least the obtained data and their associated second accurate times from the implantable medical device.

4. The method of claim 1, further comprising storing a log within the implantable medical device comprising at least the obtained data and their associated second accurate times.

5. The method of claim 1, wherein data is obtained in the implantable medical device at periodic intervals.

6. The method of claim 1, wherein the implantable medical device receives first accurate times from the external device when communication is initiated between the external device and the implantable medical device.

7. A method implementable in an implantable medical device system comprising an external device and an implantable medical device, the method comprising:
    obtaining data in the implantable medical device at various points in time;
    associating each obtained data with an inaccurate time stamp provided by the implantable medical device;
    receiving at the implantable medical device first accurate times from the external device at various points in time;
    associating each received first accurate time with an inaccurate time stamp provided by the implantable medical device;
    determining a relationship between the received first accurate times their associated inaccurate time stamps; and
    applying the relationship to the inaccurate time stamps associated with the obtained data to estimate second accurate times for each obtained data.

8. The method of claim 7, wherein the time stamps are inaccurate because they contain discontinuities indicative of reset conditions in the implantable medical device.

9. The method of claim 7, wherein the external device comprises an external controller for the implantable medical device.

10. The method of claim 7, further comprising transmitting at least the obtained data and their associated second accurate times from the implantable medical device to the external device.

11. The method of claim 7, further comprising storing a log within the implantable medical device comprising at least the obtained data and their associated second accurate times.

12. The method of claim 11, further comprising transmitting the log to another device external to the implantable medical device different from the external device.

13. The method of claim 7, wherein data is obtained in the implantable medical device at periodic intervals.

14. The method of claim 7, wherein the implantable medical device receives first accurate times from the external device when communication is initiated between the external device and the implantable medical device.

15. A method implementable in an implantable medical device system comprising an external device and an implantable medical device, the method comprising:
    storing a log in the implantable medical device, the log comprising a plurality of sequences in chronological order,
        wherein at least one sequence comprises data from the implantable device associated with an inaccurate time stamp provided by the implantable medical device, and
        wherein at least one sequence comprises a first accurate time received from the external device associated with an inaccurate time stamp provided by the implantable medical device;
    using a relationship between the first accurate times their associated inaccurate time stamps to estimate second accurate times for each obtained data; and
    storing the second accurate times with their associated data in the log.

16. The method of claim 15, wherein the log is stored in a non-volatile memory in the implantable medical device.

17. The method of claim 15, wherein the log is transmitted to the external device, and wherein the external device estimates second accurate times for each obtained data.

18. The method of claim 15, wherein the second accurate times are estimated in the implantable medical device.

19. The method of claim 15, wherein each sequence further comprises a sequence number provided by the implantable medical device.

20. A method implementable in an implantable medical device system comprising an external device and an implantable medical device, the method comprising:
    obtaining data in the implantable medical device at various points in time;
    associating time stamps provided by the implantable medical device with each obtained data to establish a time basis for the obtained data, wherein the time stamps contain chronological discontinuities indicative of reset conditions in the implantable medical device;
    receiving at the implantable medical device a first accurate time from the external device at various points in time; and
    associating each received first accurate time with a time stamp provided by the implantable medical device;
    using the first accurate times to correct the chronological discontinuities in the time basis for the data.

21. The method of claim 20, further comprising identifying the reset conditions in the time stamps, and independently correcting the time basis for the data in each region between the reset conditions.

22. The method of claim 21, wherein correcting the time basis for the data in a given region comprises establishing a relationship between the first accurate times and their associated time stamps only within the given region.

23. The method of claim 21, wherein correcting the time basis for the data in a given region comprises using at least one relationship between the first accurate times and their associated time stamps in at least one region outside the given region.

24. A system, comprising:
    an external device for wirelessly communicating with an implantable medical device, the external device comprising timing circuitry for providing an accurate time to the implantable medical device; and
    an implantable medical device, comprising a plurality of stored sequences,
        wherein at least one sequence comprises data from the implantable device associated with an inaccurate time stamp provided by timing circuitry in the implantable medical device, and
        wherein at least one sequence comprises a first accurate time received from the external device associated with an inaccurate time stamp provided by timing circuitry in the implantable medical device.

25. The system of claim 24, wherein the implantable medical device comprises an implantable neurostimulator.

26. The system of claim 24, wherein the timing circuitry in the implantable medical device does not comprise a crystal oscillator based timing circuit.

27. The system of claim 24, wherein the timing circuitry in the implantable medical device resets upon loss of power to the implantable medical stimulator.

28. The system of claim 24, wherein the implantable medical device further comprises a rechargeable battery.

29. The system of claim 24, further comprising logic circuitry for analyzing the sequences and for estimating accurate times for the data based on the analysis of the sequences.

30. The system of claim 29, wherein logic circuitry is in the implantable medical device.

31. The system of claim 29, wherein logic circuitry is in the external device.

32. A method implementable in an implantable medical device, the method comprising:
  obtaining data in the implantable medical device at various points in time;
  associating each obtained data with a time stamp provided by the implantable medical device, wherein the time stamps are inaccurate because they contain chronological discontinuities indicative of reset conditions in the implantable medical device;
  receiving at the implantable medical device first accurate times from an external device at various points in time; and
  estimating second accurate times for each obtained data using the first accurate times, wherein the second accurate times do not contain chronological discontinuities.

33. A method implementable in an implantable medical device system comprising an external device and an implantable medical device, the method comprising:
  obtaining data in the implantable medical device at various points in time;
  associating each obtained data with a time stamp provided by the implantable medical device, wherein the time stamps contain discontinuities indicative of reset conditions in the implantable medical device;
  receiving at the implantable medical device first accurate times from the external device at various points in time;
  associating each received first accurate time with a time stamp provided by the implantable medical device;
  determining a relationship between the received first accurate times their associated time stamps; and
  applying the relationship to the time stamps associated with the obtained data to estimate second accurate times for each obtained data.

34. A method implementable in an implantable medical device system comprising an external device and an implantable medical device, the method comprising:
  obtaining data in the implantable medical device at various points in time;
  associating each obtained data with a time stamp provided by the implantable medical device;
  receiving at the implantable medical device first accurate times from the external device at various points in time;
  associating each received first accurate time with a time stamp provided by the implantable medical device;
  determining a relationship between the received first accurate times their associated time stamps; and
  applying the relationship to the time stamps associated with the obtained data to estimate second accurate times for each obtained data;
  storing a log within the implantable medical device comprising at least the obtained data and their associated second accurate times; and
  transmitting the log to another device external to the implantable medical device different from the external device.

35. A method implementable in an implantable medical device system comprising an external device and an implantable medical device, the method comprising:
  storing a log in the implantable medical device, the log comprising a plurality of sequences in chronological order, each sequence comprising
    either data from the implantable medical device or a first accurate time received from the external device,
    a time stamp provided by the implantable medical device, and
    a sequence number provided by the implantable medical device;
  using a relationship between the first accurate times their time stamps to estimate second accurate times for each obtained data; and
  storing the second accurate times with their associated data in the log.

* * * * *

UNITED STATES PATENT AND TRADEMARK OFFICE
CERTIFICATE OF CORRECTION

PATENT NO. : 8,065,019 B2 Page 1 of 1
APPLICATION NO. : 12/272861
DATED : November 22, 2011
INVENTOR(S) : Goran N. Marnfeldt and Jordi Parramon It is certified that error appears in the above-identified patent and that said Letters Patent is hereby corrected as shown below:

IN THE CLAIMS:

Column 10, line 9, in Claim 15, after "times" insert --and--.

Signed and Sealed this
Thirty-first Day of January, 2012

David J. Kappos
*Director of the United States Patent and Trademark Office*